United States Patent
Jiang et al.

(10) Patent No.: US 10,460,833 B2
(45) Date of Patent: Oct. 29, 2019

(54) METHOD FOR STORING DATA OF PHOTOELECTRICALLY SYNCHRONOUS BRAIN ACTIVITY RECORDING

(71) Applicant: Institute of Automation Chinese Academy of Sciences, Beijing (CN)

(72) Inventors: Tianzi Jiang, Beijing (CN); Nianming Zuo, Beijing (CN); Xin Zhang, Beijing (CN); Yujin Zhang, Beijing (CN); Hao Liu, Beijing (CN)

(73) Assignee: INSTITUTE OF AUTOMATION CHINESE ACADEMY OF SCIENCES, Beijing (CN)

( * ) Notice: Subject to any disclaimer, the term of this patent is extended or adjusted under 35 U.S.C. 154(b) by 290 days.

(21) Appl. No.: 15/512,781

(22) PCT Filed: Sep. 19, 2014

(86) PCT No.: PCT/CN2014/086904
§ 371 (c)(1),
(2) Date: Mar. 20, 2017

(87) PCT Pub. No.: WO2016/041187
PCT Pub. Date: Mar. 24, 2016

(65) Prior Publication Data
US 2017/0290524 A1    Oct. 12, 2017

(51) Int. Cl.
*G16H 10/00* (2018.01)
*A61B 5/00* (2006.01)
(Continued)

(52) U.S. Cl.
CPC ............... *G16H 10/00* (2018.01); *A61B 5/00* (2013.01); *A61B 5/0476* (2013.01);
(Continued)

(58) Field of Classification Search
None
See application file for complete search history.

(56) References Cited

U.S. PATENT DOCUMENTS

| | | | |
|---|---|---|---|
| 8,396,525 B2 | 3/2013 | Ishikawa et al. | |
| 2004/0082862 A1* | 4/2004 | Chance ................ | A61B 5/0059 600/473 |

(Continued)

FOREIGN PATENT DOCUMENTS

| | | |
|---|---|---|
| CN | 102715889 A | 10/2012 |
| CN | 102779229 A | 11/2012 |

(Continued)

*Primary Examiner* — Etsub D Berhanu
(74) *Attorney, Agent, or Firm* — Howard IP Law, PLLC; Jeremy Howard

(57) ABSTRACT

A method for storing data of photoelectrically synchronous brain activity recording, said method comprising: generating data when a photoelectrically synchronous brain activity detection system is operating; generating from said data a data storage file comprising a basic information data segment, a near-infrared spectrum data segment and a brain electrical activity data segment, and sequentially storing said data segments into a .neg file in binary form according to the above order. The method can store comprehensive test information, flexibly configure the near-infrared and brain electrical measurement information, and realize synchronous storage of near-infrared data and brain electrical data and maintain file version compatibility.

6 Claims, 4 Drawing Sheets

(51) Int. Cl.
  *A61B 5/0476*   (2006.01)
  *G06F 3/06*     (2006.01)
  *A61B 5/1455*   (2006.01)
  *G16H 40/63*    (2018.01)
  *G16H 10/60*    (2018.01)

(52) U.S. Cl.
  CPC ........ *A61B 5/14553* (2013.01); *G06F 3/0643* (2013.01); *G16H 10/60* (2018.01); *G16H 40/63* (2018.01)

(56) References Cited

U.S. PATENT DOCUMENTS

| 2005/0043827 A1* | 2/2005 | Schaeffer ............... G06Q 10/10 700/72 |
| 2005/0086166 A1* | 4/2005 | Monk .................... G06Q 20/04 705/41 |
| 2014/0171757 A1 | 6/2014 | Kawato |

FOREIGN PATENT DOCUMENTS

| CN | 103838736 A | 6/2014 |
| CN | 103917268 A | 7/2014 |
| JP | 2006-289565 A | 10/2006 |

* cited by examiner

METHOD FOR STORING DATA OF PHOTOELECTRICALLY SYNCHRONOUS BRAIN ACTIVITY RECORDING

TECHNICAL FIELD

The present invention relates to a data storage method, in particular to a method for storing data of photoelectrically synchronous brain activity recording.

BACKGROUND OF THE INVENTION

Brain functional activities include several procedures like neuronal activity and local energy metabolism, and complicated functional activities enable the brain to bring together information of multiple modes, among which electrical activities of neurons and changes in blood oxygen metabolism in active areas are the most important, and only by effectively extracting, analyzing and mixing said two kinds of information, can the brain functional activities be organically linked to each other. A photoelectrically synchronous brain activity detection system intends to realize integration of the three functions of near-infrared spectrometer, electroencephalograph and fusion device of near-infrared spectrometer and electroencephalograph on one instrument through an effective combination of the fNIRS (functional near-infrared spectroscopy) technology and the EEG acquisition technology, thereby realizing functions like synchronizing or separate collecting of the neural electrical activity and blood oxygen supply information in brain areas. The combination of the NIRS (near-infrared spectroscopy) technology and the EEG acquisition technology implies synchronous collection of optical and electrical signals, and the collected data need to be stored synchronously, so it requires that not only the photoelectric signals should be consistent in time scale and space, but also the data storage files should have compatibility.

So far, there has not been any photoelectrically synchronous detection device or system at home and abroad yet, let alone data storage files for such device or system, nor has any corresponding patent been found. With the progress achieved in science and technology in recent years and out of the urgent clinical needs, there are more and more basic researches and application researches on combining the EEG technology and the near-infrared technology, so there is the need for designing a data storage file format for a photoelectrically synchronous brain activity detection system, which can be used to synchronously store the collected brain electrical signals and near-infrared signals.

SUMMARY OF THE INVENTION

The object of the present invention is to provide a data storage method to overcome the defect of the prior art, which can realize synchronous storage of brain electrical signals and near-infrared signals by means of a simple and reliable data storage file format.

In order to achieve the above-mentioned object, the present invention provides a method for storing data of photoelectrically synchronous brain activity recording, said method comprises:

generating data when a photoelectrically synchronous brain activity detection system is operating;

generating from said data a data storage file comprising a basic information data segment, a near-infrared spectrum data segment and a brain electrical activity data segment, and sequentially storing said data segments into a .neg file in binary form according to the above order;

wherein the basic information data segment includes mode information, file version number, name and ID number of a tested person, doctor's name and workplace, and age and name of a tested person;

the near-infrared spectrum data segment includes:

a near-infrared data basic information field, which includes a sampling frequency of a near-infrared signal, a total number of event stimulations, a near-infrared wavelength, number of channels, number and positions of light sources, number and positions of probes, and number of samples of near-infrared data;

a near-infrared data channel information field, which includes a valid flag bit of the channel, a light source index, a probe index, an analog magnification of the probe, a digital magnification of the probe and a reference light density;

a near-infrared data measurement data field, which includes a collected near-infrared spectral density;

a near-infrared data event stimulation field, which includes an event stimulation name, a stimulation type, and a flag position.

The brain electrical activity data segment includes:

a brain electrical data basic information field, which includes a brain electrical signal sampling frequency, number of channels, a total number of event stimulations, start and stop signs of low-pass filtering of an amplifier, start and stop signs of high-pass filtering of an amplifier, a reference electrode sign and a sample number;

a brain electrical data channel information field, which includes a channel valid flag bit, an excitation electrode index, a measurement electrode index, an analog magnification of a measurement electrode, and a digital magnification of the measurement electrode;

a brain electrical data measurement data field, which includes the collected brain electrical signals;

a brain electrical data event stimulation field, which includes an event stimulation name, a stimulation type, and a flag position.

Further, said basic information data field includes a basic data type check bit and a file version number, and can automatically call corresponding interfaces for extracting test data according to different check bits.

Further, the near-infrared signal and brain electrical signal are collected synchronously and are stored in a file simultaneously for synchronous storage of data.

Further, said near-infrared data basic information field records basic information of a near-infrared test sensor, including positions of the light source and the detector and the number of channels.

Further, said near-infrared data channel information data segment includes near-infrared light source and probe index information for configuring the near-infrared light source and probe information.

Further, said near-infrared measurement data segment and brain electrical activity measurement data segment dynamically access near-infrared data and brain electrical data, including lead number, time length, experiment task design, according to the number of samples in the near-infrared data basic information field and the brain electrical activity basic information field.

The method for storing data of photoelectrically synchronous brain activity recording according to the present invention can store comprehensive test information, flexibly configure the near-infrared and brain electrical measurement information, and realize synchronous storage of near-infrared data and brain electrical data and maintain file version compatibility.

DETAILED DESCRIPTION OF THE INVENTION

The technical solution of the present invention will be described in further detail below in conjunction with the drawings and embodiments.

Figure 1:
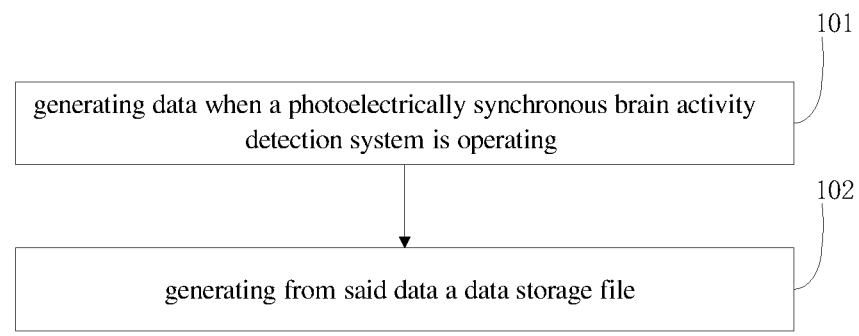
FIG. 1 is a flow chart of the method for storing data of photoelectrically synchronous brain activity recording according to the present invention.

FIG. 1 is a flow chart of the method for storing data of photoelectrically synchronous brain activity recording according to the present invention. As shown in the figure, the method comprises the following steps:

step 101: generating data when a photoelectrically synchronous brain activity detection system is operating;

step 102: generating a data storage file from said data.

Figure 2:
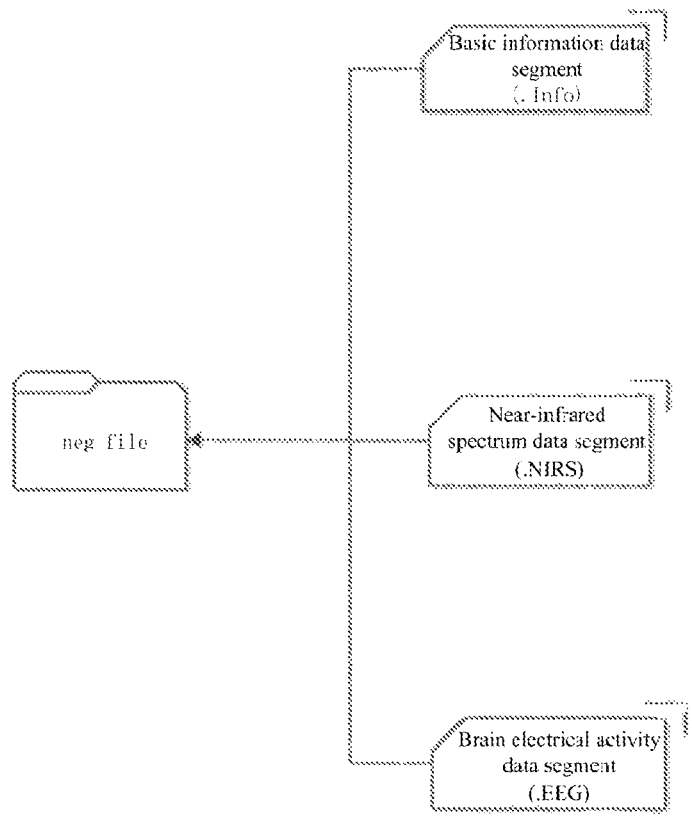
FIG. 2 is a schematic drawing of the data storage file of the present invention.

According to the schematic drawing of the data storage file of the present invention as shown in FIG. 2, the data storage file comprises a basic information data segment, a near-infrared spectrum data segment and a brain electrical activity data segment, and said data segments are sequentially stored into a .neg file in binary form according to the above order.

By writing the basic information data segment, the near-infrared spectrum data segment, the brain electrical activity data segment, etc. as a whole into a .neg file in binary form, the file access speed can be increased while ensuring completeness of all information.

Figure 3:
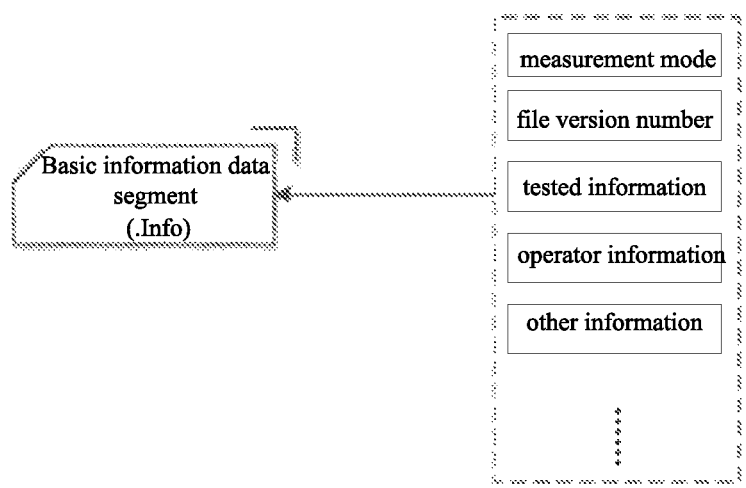
FIG. 3 is a structural diagram of the basic information data segment (.Info) of the present invention.

According to the structural diagram of the basic information data segment (.Info) of the present invention as shown in FIG. 3, the basic information data segment includes mode information, file version number, name and ID number of a tested person, doctor's name and workplace, and age and name of a tested person.

Said data segment includes information like the file version number, and systems of different versions can automatically call corresponding interfaces for extracting test data according to different file version numbers, thus improving file compatibility and facilitating data reading operations among different systems.

The basic information data field includes not only a basic data type check bit, but also a file version number, and the system can automatically call corresponding interfaces for extracting test data according to different check bits, thus improving file compatibility and facilitating data reading operations among different systems.

Figure 4:
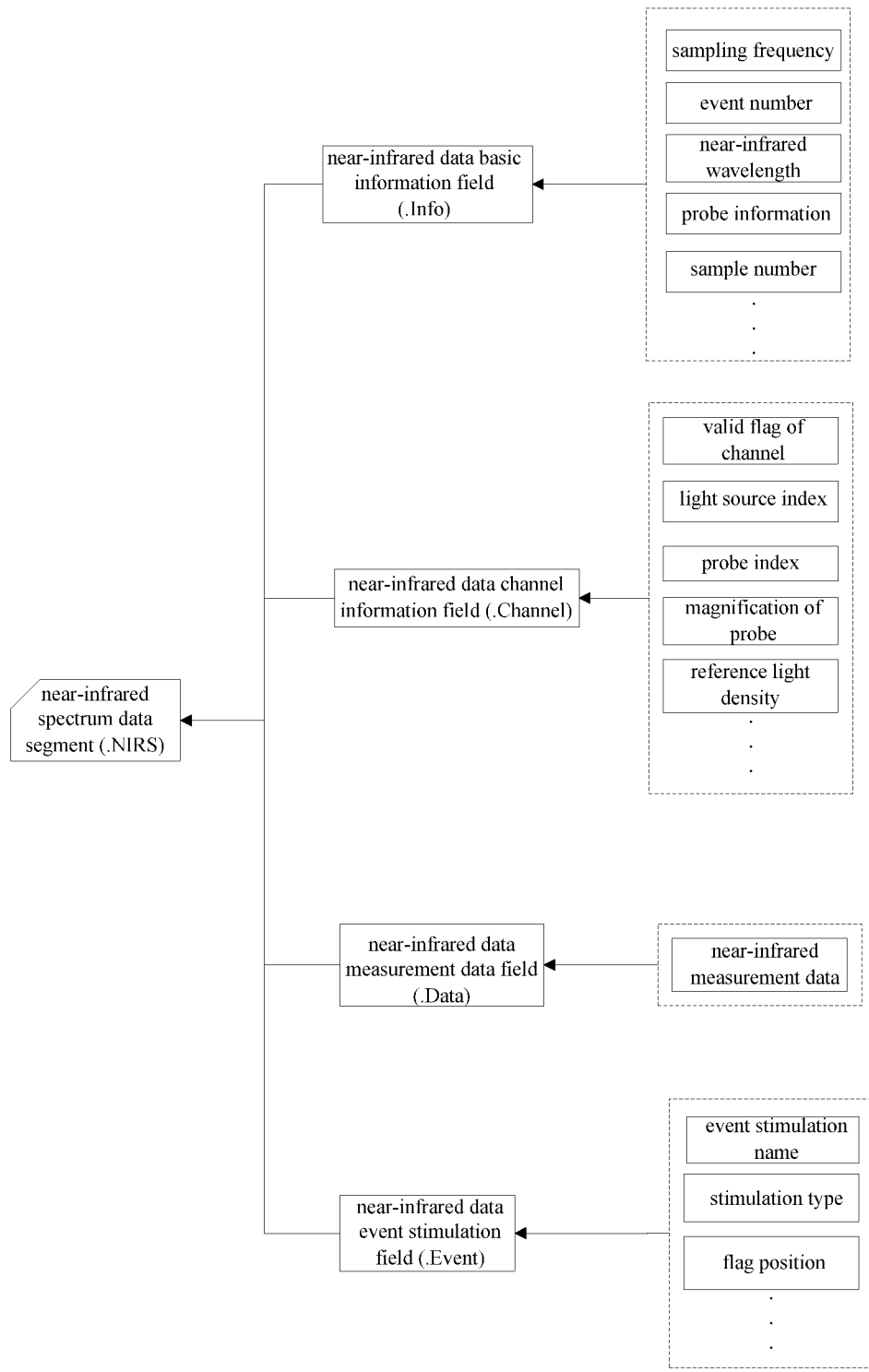
FIG. 4 is a structural diagram of the near-infrared spectrum data segment (.NIRS) of the present invention.

According to the structural diagram of the near-infrared spectrum data segment (.NIRS) of the present invention as shown in FIG. 4, the near-infrared spectrum data segment includes:

1. a near-infrared data basic information field, which includes a sampling frequency of a near-infrared signal, a total number of event stimulations, a near-infrared wavelength, number of channels, number and positions of light sources, number and positions of probes, and number of samples of near-infrared data;

2. a near-infrared data channel information field, which includes a valid flag bit of the channel, a light source index, a probe index, an analog magnification of the probe, a digital magnification of the probe and a reference light density;

3. a near-infrared data measurement data field, which includes a collected near-infrared spectral density;

4. a near-infrared data event stimulation field, which includes an event stimulation name, a stimulation type, and a flag position.

The near-infrared spectrum data segment (.NIRS) is divided into the four parts of a near-infrared data basic information field (.Info), a near-infrared data channel information field (.Channel), a near-infrared data measurement data field (.Data), and a near-infrared data event stimulation field (.Event). The near-infrared data basic information field (.Info) includes basic information of a near-infrared test sensor, such as positions of light source and detector, number of channels, etc., which enables the system to conveniently read the configuration information of the near-infrared device; the near-infrared data channel information field (.Channel) includes basic information of the channel, and the system can flexibly configure the near-infrared data collection channel according to said field; the near-infrared data measurement data field (.Data) consists of collected near-infrared light densities; and the near-infrared data event stimulation field (.Event) records basic information of event stimulation, such as name, position, etc.

The near-infrared basic information data field records basic information of the near-infrared test sensor, such as positions of light source and detector, number of channels, etc., which enables the system to conveniently read the configuration information of the near-infrared device.

The near-infrared data channel information data segment includes near-infrared light source and probe index information, thus allowing the system to flexibly configure the near-infrared light source and probe information.

The near-infrared measurement data segment and brain electrical activity measurement data segment can dynamically access near-infrared data and brain electrical data, including lead number, time length, experiment task design, etc., according to the number of samples in the near-infrared basic information data field and the brain electrical activity basic information field.

Figure 5:
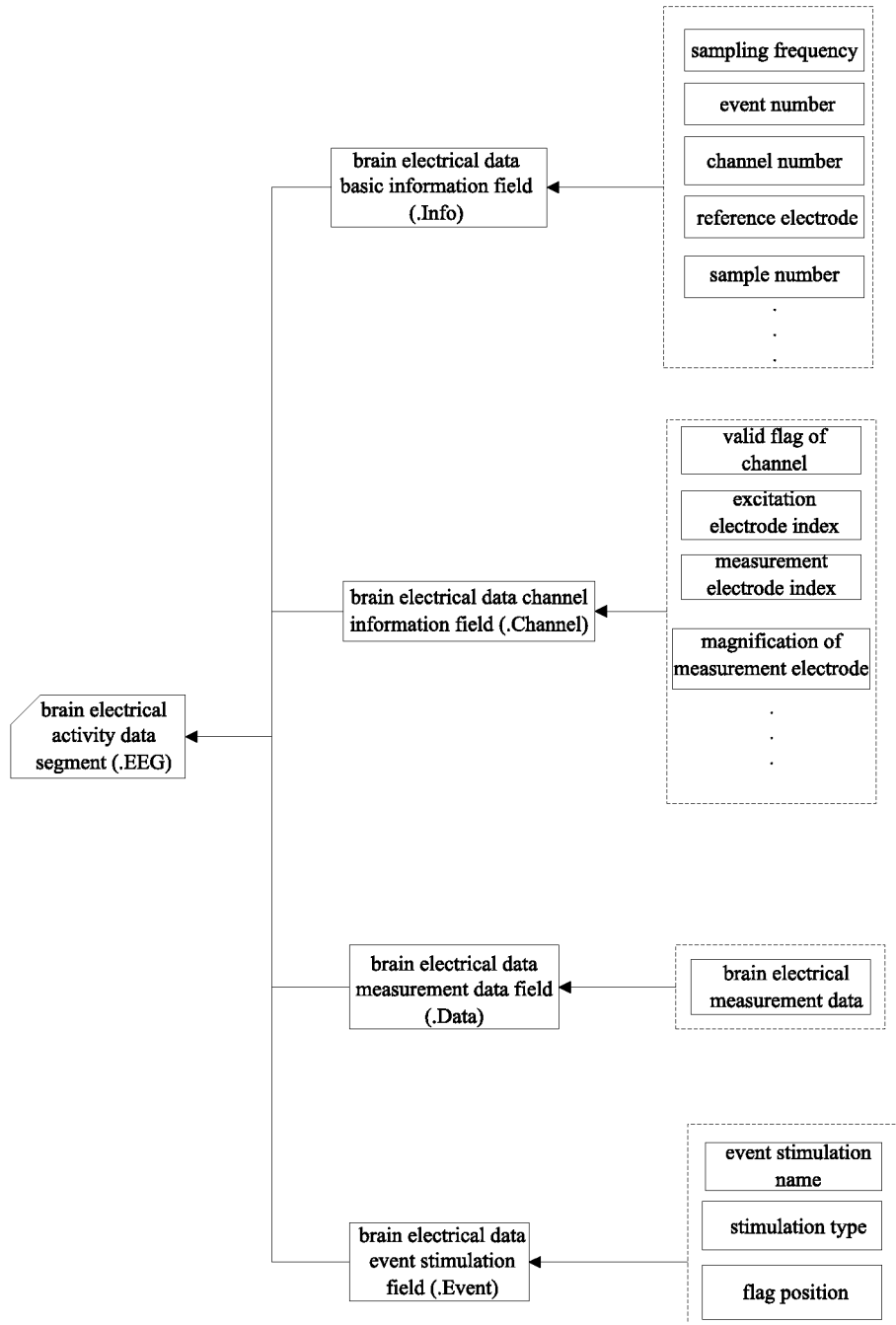
FIG. 5 is a structural diagram of the brain electrical activity data segment (.EEG) of the present invention.

According to the structural diagram of the brain electrical activity data segment (.EEG) of the present invention as shown in FIG. 5, the brain electrical activity data segment includes:

1. a brain electrical data basic information field, which includes a brain electrical signal sampling frequency, number of channels, a total number of event stimulation, start and stop signs of low-pass filtering of an amplifier, start and stop signs of high-pass filtering of an amplifier, a reference electrode sign and a sample number;

2. a brain electrical data channel information field, which includes a channel valid flag bit, an excitation electrode index, a measurement electrode index, an analog magnification of the measurement electrode, and a digital magnification of the measurement electrode;

3. a brain electrical data measurement data field, which includes the collected brain electrical signals;

The brain electrical data event stimulation field includes an event stimulation name, a stimulation type, and a flag position.

Said data segment can be further divided into the four parts of a brain electrical data basic information field (.Info), a brain electrical data channel information field (.Channel), a brain electrical data measurement data field (.Data), and a brain electrical data event stimulation field (.Event). Wherein the brain electrical data basic information field (.Info) includes a brain electrical data sampling frequency, number of channels, an event number, a reference electrode, etc., and the system can quickly read the basic information of the brain electrical data according to said field; the brain electrical data channel information field (.Channel) includes basic information of the channel, such as an electrode index, etc., and the system can flexibly configure the brain electrical acquisition channel according to said field; the brain electrical data measurement data field (.Data) consists of the collected brain electrical signals; and the brain electrical data event stimulation field (.Event) records basic information of event stimulation, such as name, position, etc.

By simultaneously storing the near-infrared signals and brain electrical signals synchronously collected by the brain activity detection system in the file, synchronous storage of data is realized, which can help maintaining consistency and synchronization between the near-infrared signals and the brain electrical signals.

The method for storing data of photoelectrically synchronous brain activity recording according to the present invention can store abundant test information, flexibly configure the near-infrared and brain electrical measurement information, and realize synchronous storage of near-infrared data (NIRS data) and brain electrical data (EEG data) and maintain file version compatibility.

Those skilled in the art shall be aware that the exemplary units and algorithm steps described in conjunction with the embodiments disclosed herein can be realized by electronic hardware, computer software or a combination thereof, and in order to clearly illustrate the interchangeability between the hardware and software, the exemplary components and steps have been generally described above in terms of the functions thereof. As for whether said functions should be achieved by hardware or by software, it depends on the specific application and restrictions of design of the technical solution. Those skilled in the art can use a different method for each specific application so as to achieve the described functions, but such implementation shall not be considered as going beyond the scope of the present invention.

The steps of method or algorithm described in conjunction with the embodiments disclosed herein can be carried out by hardware, software modules executed by a processor or by a combination thereof. The software modules can be disposed in a random access memory (RAM), a memory, a read-only memory (ROM), an electrically-programmable ROM, an electrically erasable programmable ROM, a register, a hard disc, a removable disc, a CD-ROM or any other form of storage medium known in the art.

The above-described specific embodiment describes in detail the object, technical solution and advantageous effect of the present invention. But it shall be appreciated that all the above described are merely specific embodiments of the present invention, which do not intend to limit the protection scope of the invention. Any modification, equivalent substitution and improvement made under the spirit and principle of the present invention shall fall within the protection scope of the present invention.

What is claimed is:

1. A method for storing data of photoelectrically synchronous brain activity recordings, characterized in that said method comprises:

generating data when a photoelectrically synchronous brain activity detection system is operating;

generating from said data a data storage file comprising a basic information data segment, a near-infrared spectrum data segment and a brain electrical activity data segment, and storing said data segments into a .neg file in binary form;

wherein the basic information data segment includes mode information, file version number, name and ID number of a tested person, doctor's name and workplace, and age and name of a tested person;

the near-infrared spectrum data segment includes:

a near-infrared data basic information field, which includes a sampling frequency of a near-infrared signal, a total number of event stimulations, a near-infrared wavelength, number of channels, number and positions of light sources, number and positions of probes, and number of samples of near-infrared signals;

a near-infrared data channel information field, which includes a valid flag bit of the channel, a light source index, a probe index, an analog magnification of each probe, a digital magnification of each probe and a reference light density;

a near-infrared data measurement data field, which includes a collected near-infrared spectral density; and a near-infrared data event stimulation field, which includes an event stimulation name, a stimulation type, and a flag position; and the brain electrical activity data segment includes:

a brain electrical data basic information field, which includes a brain electrical signal sampling frequency, number of channels, a total number of event stimulations, start and stop signs of low-pass filtering of an amplifier, start and stop signs of high-pass filtering of an amplifier, a reference electrode sign and the number of samples of collected brain electrical signals;

a brain electrical data channel information field, which includes a channel valid flag bit, an excitation electrode index, a measurement electrode index, an analog magnification of a measurement electrode, and a digital magnification of the measurement electrode;

a brain electrical data measurement data field, which includes the collected brain electrical signals; and a brain electrical data event stimulation field, which includes an event stimulation name, a stimulation type, and a flag position.

2. The method according to claim 1, characterized in that said basic information data segment includes a basic data type check bit and a file version number, and can automatically call corresponding interfaces for extracting test data according to different check bits.

3. The method according to claim 1, characterized in that said near-infrared signals and said brain electrical signals are collected synchronously and are stored in a file simultaneously for synchronous storage of data.

4. The method according to claim 1, characterized in that said near-infrared data basic information field records basic information of a near-infrared test sensor, including positions of each light source and the near-infrared test sensor and the number of channels.

5. The method according to claim 1, characterized in that said near-infrared data channel information field includes near-infrared light source and probe index information.

6. The method according to claim 1, characterized in that said near-infrared data measurement data field and said brain electrical data measurement data field dynamically access said near-infrared signals and said brain electrical signals, according to the number of samples in the near-infrared data basic information field and the brain electrical data basic information field.

\* \* \* \* \*